(12) United States Patent
Shanklin et al.

(10) Patent No.: US 9,976,155 B2
(45) Date of Patent: *May 22, 2018

(54) ACCUMULATION OF OMEGA-7 FATTY ACIDS IN PLANT SEEDS

(71) Applicants: Brookhaven Science Associates, LLC, Upton, NY (US); Dow AgroSciences LLC, Indianapolis, IN (US)

(72) Inventors: John Shanklin, Shoreham, NY (US); Tam Huu Nguyen, Lincoln, NE (US); Terence A. Walsh, Zionsville, IN (US); Mark S. Pidkowich, British Colombia (CA); Edward J. Whittle, Greenport, NY (US)

(73) Assignees: Dow AgroSciences LLC, Indianapolis, IN (US); Brookhaven Science Associates, LLC, Upton, NY (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/130,788

(22) Filed: Apr. 15, 2016

(65) Prior Publication Data

US 2016/0272986 A1 Sep. 22, 2016

Related U.S. Application Data

(62) Division of application No. 13/168,320, filed on Jun. 24, 2011, now Pat. No. 9,340,776.

(60) Provisional application No. 61/358,318, filed on Jun. 24, 2010.

(51) Int. Cl.
*C12N 15/82* (2006.01)
*C12N 9/02* (2006.01)

(52) U.S. Cl.
CPC ....... *C12N 15/8247* (2013.01); *C12N 9/0071* (2013.01); *C12N 9/0083* (2013.01); *C12Y 114/19001* (2013.01)

(58) Field of Classification Search
None
See application file for complete search history.

(56) References Cited

U.S. PATENT DOCUMENTS

| | | | |
|---|---|---|---|
| 5,866,789 A | 2/1999 | Hildebrand et al. | |
| 7,109,392 B1 | 9/2006 | Broglei et al. | |
| 7,323,335 B2 | 1/2008 | Shanklin et al. | |
| 7,964,403 B2 | 6/2011 | Mihaliak et al. | |
| 2005/0005325 A1* | 1/2005 | Shanklin | C12N 15/8247 800/281 |
| 2005/0039234 A1* | 2/2005 | Heilmann | C07H 21/04 800/287 |
| 2005/0130284 A1 | 6/2005 | Milcamps et al. | |
| 2008/0118623 A1 | 5/2008 | Damude et al. | |
| 2008/0274259 A1 | 11/2008 | Damude et al. | |

FOREIGN PATENT DOCUMENTS

| | | |
|---|---|---|
| CA | 2376056 | 12/2000 |
| CN | 101065013 | 10/2007 |
| WO | 200075170 | 12/2000 |
| WO | 2006042049 | 4/2006 |

OTHER PUBLICATIONS

Thelen et al (2002 Metabolic Engineering 4: p. 12-21). Already of record.*
Kunst et al 1989 (Plant Physiology 90: p. 943-947).*
Bondaruk, M. et al., "Expression of a cDNA encoding palmitoyl-acyl carrier protein desaturase form cat's claw (*Doxantha unguis-cati* L.) in *Arabidopsis thaliana* and *Brassica napus* leads to accumulation of unusual unsaturated fatty acids and increased stearic acid content in the seed oil," Plant Breeding, 2007 pp. 186-194, vol. 126.
Covello et al., "Functional Expression of the Extraplastidial *Arabidopsis thaliana* Oleate Desaturase Gene (FAD2) in Saccharmyces cerevisiae" Plant Physiol. (1996), vol. 111, pp 223-226.
David J. Schultz et al. Expression of a A9 14:0-acyl carrier proteinfatty acid desaturase gene is necessary for the production of m5 anacardic acids found in pest-resistant geranium (Pelargonium xhortorum). Proc. Natl. Acad. Sci. USA. 1996, vol. 93, pp. 8771-8775.
GenBank Accession No. XM_002531843, Ricinus communis Stearoy—ACP desaturase, mRNA, Aug. 6, 2009.
GenBank Database accession No. ADW26131, Mar. 24, 2005.
GenBank Database Accession No. ADW26171, Mar. 24, 2005.
Guo et al (PNAS(2004) 101: 9205-9210).
International Search Report of International Application No. PCT/US2011/041759, dated Feb. 23, 2012.
Shanklin, Lou Y., et al., "Evidence that the yeast desaturase Ole1p exist dimer in vivo," The Hournal of Biological Chemistry, pp. 19384-19390, vol. 285, No. 25.
Supplementary European Search Report for EP 11798970, dated Oct. 24, 2013, 2 pages.
Thelen et al. 2002 Metabolic Engineering 4: p. 12-21.
Wang "Expression of the yeast Delta-9 desaturase gene in tomato enhances its resistance to powdery mildew." Physiological and molecular plant pathology, 1998, vol. 52 pp. 37-383.

(Continued)

*Primary Examiner* — Matthew R Keogh

(74) *Attorney, Agent, or Firm* — Marcia I. Rosenfeld; Magleby Cataxinos & Greenwood

(57) ABSTRACT

Compositions and methods include genetically encoding and expressing a novel $\Delta^9$-18:0-ACP desaturase in plant cells. In some embodiments, nucleic acid molecules encode the novel $\Delta^9$-18:0-ACP desaturase. In other embodiments, amino acid sequences have $\Delta^9$-18:0-ACP desaturase activity. Methods can involve expression of $\Delta^9$-18:0-ACP desaturase in plant cells, plant materials, and whole plants for the purpose of increasing the amount of unusual fatty acids in whole plants, plant seeds, and plant materials, for example, seeds.

16 Claims, 5 Drawing Sheets

(56) References Cited

OTHER PUBLICATIONS

Whittle, Edward et al., "Engineering Δ9-16:0-Acyl carrier protein (ACP) desaturase specificity based on combinatorial saturation mutagenesis and logical redesign of the caster Δ9-18:0-ACP desaturase," The Journal of Biological Chemistry, Jun. 15, 2001, pp. 21500-21505, vol. 276, No. 24.

Written Opinion of the International Application No. PCT/US2011/041759, dated Feb. 23, 2012.

* cited by examiner

ACCUMULATION OF OMEGA-7 FATTY ACIDS IN PLANT SEEDS

CROSS-REFERENCE TO RELATED APPLICATION

This application is a divisional of U.S. patent application Ser. No. 13/168,320 filed Jun. 24, 2011, which claims the benefit of U.S. Provisional Patent Application Ser. No. 61/358,318, filed Jun. 24, 2010, the disclosure of each are hereby incorporated herein in their entirety by this reference.

This invention was made under a CRADA (BNL-C-05-11) between DOW Agrosciences LLC and Brookhaven Science Associates, LLC operated for the United States Department of Energy. The Government has certain rights in this invention.

FIELD OF THE INVENTION

In particular embodiments, the invention relates to a novel mutant *Ricinus* $\Delta^9$-18:0-ACP desaturase, designated Com25, that functions as a $\Delta^9$-16:0-ACP desaturase. Another embodiment relates to methods of metabolic engineering to manipulate metabolic branch points in plants, for example, to redirect carbon into ω-7 fatty acids. In certain embodiments, the invention relates to methods for expressing Com25 as part of a metabolic engineering strategy, such that carbon is redirected into ω-7 fatty acids in plant seeds.

BACKGROUND

It has been estimated that there may be upwards of 1,000 fatty acid structures in nature. Millar et al., (2000) Trends Plant Sci 5(3):95-101. Many of these fatty acids are synthesized by derivatization of the fatty acids by an array of variants of archetypal desaturases. The first of these variant desaturases to be isolated was the *Ricinus* oleate hydroxylase from castor endosperm, the enzyme responsible for ricinoleic acid synthesis. van de Loo et al., (1995) Proc. Natl. Acad. Sci. USA 92(15):6743-6747. This was followed by the genes encoding the *Vernonia* linoleate epoxidase and the *Crepis* oleate actylenase. Lee et al., (1998) Science 280(5365):915-18. The isolation of these genes led to the notion that their heterologous expression in oil crop plants could facilitate the accumulation of the corresponding unusual fatty acids. Broun et al., (1997) Plant Journal 13:201-10. However, the resulting unusual fatty acid accumulation was invariably lower than that found in the natural source plant from which the gene was isolated. Napier, J. A. (2007) Annu. Rev. Plant Biol. 58:295-319.

The specific activity profiles of variant desaturase enzymes that have been isolated from tissues that accumulate unusual fatty acids are consistent with a role of producing the corresponding unusual fatty acids. However, they exhibit very poor specific activities compared with all stearoyl-ACP desaturases reported to date and have proved ineffective in producing altered fatty acid phenotypes when heterologously expressed. Cahoon et al., (1994) Prog. Lipid Res. 33:155-63. For instance, seed-specific expression of the castor hydroxylase under the control of a strong seed-specific promoter in the model plant *Arabidopsis* resulted in the accumulation of only about 17% of ricinoleic acid, far short of the about 90% found in castor seed. Broun and Somerville (1997) Plant Physiol. 113:933-42. Similarly disappointing results have been reported for epoxy and acetylenic fatty acids which have been reported to accumulate to 15 and 25% respectively upon heterologous expression of the epoxygenase and acetylenase in *Arabidopsis*. Lee et al., (1998) Science 280(5365):915-18. In addition to showing poor activities, variant desaturases tended to form insoluble aggregates when purified. Low stability and poor catalytic rates are properties shared by many newly evolved enzymes that arise as gene duplication events in which selection for stability and/or turnover is released, while mutations accumulate that finally result in alteration of function. Govindarajan and Goldstein (1998) Proc. Natl. Acad. Sci. USA 95:5545-49; Goldstein (2001) in Protein Folding, Evolution and Design (Broglia, R. A., Shakhnovich, E. I., and Tiana, G., eds) CXLIV Vols., I.O.S. Press, Amsterdam.

Many potential explanations for low levels of target fatty acid accumulation have been advanced. Napier, J. A. (2007) Annu. Rev. Plant Biol. 58:295-319. Evidence suggests specialized enzymes may play a key role in the incorporation of the unusual fatty acid into triacylglycerols. For instance, the accumulation of laurate in transgenic *Brassica napus* seeds increased from 50% to 60% upon the coexpression of a coconut lysophosphatidic acid acyltransferase along with the California bay medium chain thioesterase. Knutzon et al., (1999) Plant Physiol. 120(3):739-46. Recently, coexpression of the castor type-2 acyl-coenzyme A:diacylglycerol acyltransferase (RcDGAT2) along with the castor hydroxylase increased the accumulation of ricinoleic acid from about 17% to about 30%. Burgal et al., (2008) Plant Biotechnol. J. 6(8):819-31.

Accumulating high levels of unusual fatty acids in transgenic plants equivalent to those found in naturally occurring species has yet to be reported. As unusual fatty acids are highly desirable in a variety of industries and applications, there is a need for better expression of unusual fatty acids in transgenic plants designed for their production.

BRIEF SUMMARY OF THE INVENTION

Disclosed herein are nucleotide sequences encoding a novel variant desaturase, designated Com25, and the amino acid sequence thereof.

Also disclosed are methods of expressing Com25 in a plant cell, to take advantage of the Com25 enzyme's enhanced desaturase activity, relative to the WT castor $\Delta^9$-18:0 desaturase, such that the percent composition of unusual fatty acids in plant seeds is increased. In some embodiments, the methods include expressing Com25 in *Arabidopsis*. In certain embodiments, the unusual fatty acids increased in plant seeds are C-7 fatty acids. In these embodiments, the ω-7 fatty acids may be $16:1\Delta^9$ and/or $18:1\Delta^{11}$.

Methods are also provided for expressing Com25 in a plant cell, wherein the plant cell is impaired in plastidial and extraplastidial fatty acid elongation, such that the percent composition of unusual fatty acids in plant seeds is increased. In some embodiments, the methods include expressing Com25 in *Arabidopsis*. In certain embodiments, the unusual fatty acids increased in plant seeds are ω-7 fatty acids. In these embodiments, the ω-7 fatty acids may be $16:1\Delta^9$ and/or $18:1\Delta^{11}$.

Further methods are provided for expressing Com25 in a plant cell wherein KASII is inhibited in the plant cell, such that the percent composition of unusual fatty acids in plant seeds is increased. In some embodiments, the methods include expressing Com25 in *Arabidopsis*. In certain embodiments, the unusual fatty acids increased in plant seeds are ω-7 fatty acids. In these embodiments, the ω-7 fatty acids may be $16:1\Delta^9$ and/or $18:1\Delta^{11}$.

Methods are also provided for expressing Com25 in a plant cell wherein KASII and plastidial and extraplastidial fatty acid elongation are inhibited in the plant cell, such that the percent composition of unusual fatty acids in plant seeds is increased. In some embodiments, the methods include expressing Com25 in *Arabidopsis*. In certain embodiments, the unusual fatty acids increased in plant seeds are ω-7 fatty acids. In these embodiments, the ω-7 fatty acids may be 16:1Δ$^9$ and/or 18:1Δ$^{11}$.

The foregoing and other features will become more apparent from the following detailed description of several embodiments, which proceeds with reference to the accompanying figures.

DETAILED DESCRIPTION

I. Overview of Several Embodiments

Figure 1:
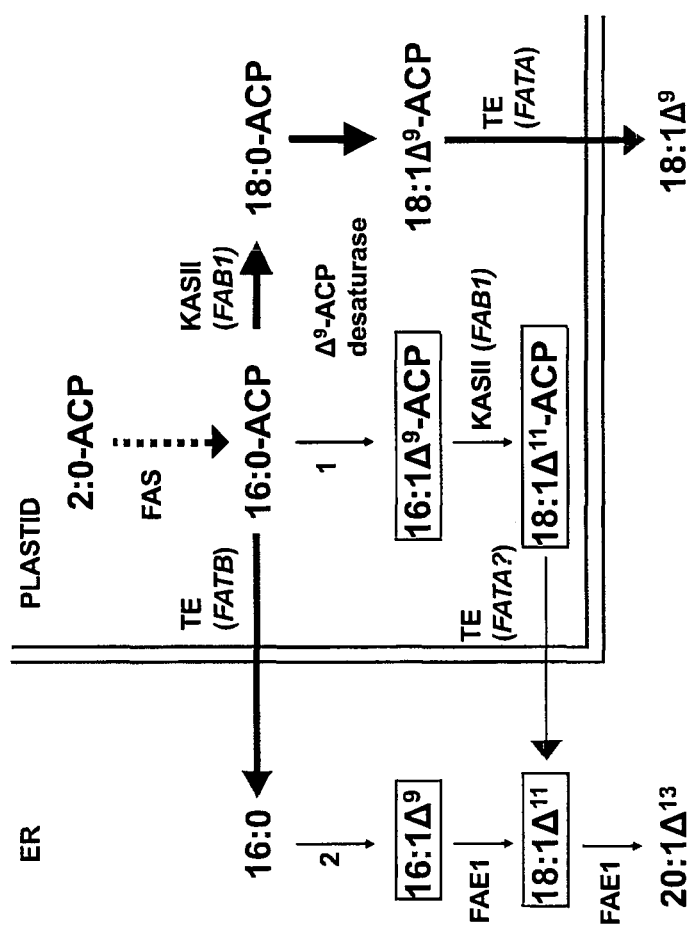
FIG. 1 depicts a schematic of fatty acid synthesis and modification in the plastid and endoplasmic reticulum of *Arabidopsis*. Reactions mediated by 16:0 desaturases are indicated 1: Δ$^9$-16:0-ACP desaturase; 2: extraplastidial Δ$^9$-16:0-ACP desaturase. ω-7 FA, i.e., 16:1 Δ$^9$ and 18:1 Δ$^{11}$ are boxed.

Disclosed herein are nucleotide acid molecules encoding a Δ$^9$ desaturase enzyme comprising a nucleotide sequence at least 60% identical to SEQ ID NO: 1. The nucleic acid molecules may further comprise a gene regulatory element. In some embodiments, the gene regulatory element may be a phaseolin promoter.

Also disclosed are Δ$^9$ desaturase enzymes comprising an amino acid sequence at least 80% identical to SEQ ID NO:2. Δ$^9$ desaturase enzymes of the present invention wherein the amino acid sequence is at least 80% identical to SEQ ID NO:2 may further comprise a serine at the position analogous to position 114 in SEQ ID NO:2; an arginine at the position analogous to position 117 in SEQ ID NO:2; a cysteine at the position analogous to position 118 in SEQ ID NO:2, a leucine at the position analogous to position 179 in SEQ ID NO:2; and/or a threonine at the position analogous to position 188 in SEQ ID NO:2.

Nucleic acid molecules and Δ$^9$ desaturase enzymes of the present invention may be expressed in plant materials, cells, tissues, or whole plants, to increase the amount of unusual fatty acids in the plant material, cells, tissues, or whole plants, relative to the amount observed in a wild type plant of the same species. Alternative embodiments of the invention include methods for increasing the amount of unusual fatty acids in the plant material, cells, tissues, or whole plants comprising transforming plant material, cells, tissues, or whole plants with the nucleic acid molecule of SEQ ID NO:1, such that the amount of unusual fatty acids in said plant material, cells, tissues, or whole plants is increased.

In preferred embodiments, the plant material, cells, tissues, or whole plants that are transformed by the disclosed methods further comprise one or more means for increasing levels of 16:0-ACP in the plant material, cells, tissues, or whole plants. In certain embodiments, the means for increasing the levels of 16:0-ACP in the plant material, cells, tissues, or whole plants may be: expression of an extraplastidial desaturase; suppression of KASII, for example by introducing a mutation in the fab1 gene; and/or decreasing the elongation of 16:0 fatty acids, for example by introducing a mutation in the fae1 gene.

Disclosed methods herein may be performed, for example, on plants, or plant materials derived from plants, of the genus *Arabidopsis*. A particular embodiment is drawn to methods for creating or regenerating a genetically engineered plant comprising increased amounts of unusual fatty acids in the plant compared to a wild type plant of the same species, comprising transforming plant material with nucleic acid molecule of SEQ ID NO: 1; and culturing the transformed plant material to obtain a plant. Plants, plant materials, plant cells, and seeds obtained by the aforementioned methods are also disclosed.

II. Abbreviations x:yΔ$^z$ fatty acid containing x carbons and y double bonds in position z counting from the carboxyl end
ACP acyl carrier protein
COA coenzyme A
KASII β-ketoacyl-ACP synthase II
FA fatty acids
FAS fatty acid synthesis
FAME fatty acid methyl ester
WT wild type III. Terms Fatty acid: As used herein, the term "fatty acid" refers to long chain aliphatic acids (alkanoic acids) of varying chain lengths, from about C12 to C22, although both longer and shorter chain-length acids are known. The structure of a fatty acid is represented by the notation, x:yΔ$^z$, where "x" is the total number of carbon (C) atoms in the particular fatty acid, and "y" is the number of double bonds in the carbon chain in the position "z," as counted from the carboxyl end of the acid.

Unusual fatty acid: For the purposes of the present invention, unusual fatty acids are those whose synthesis in natural systems is initiated by modification of an intermediate of FAS by a variant desaturase enzyme.

Metabolic pathway: The term, "metabolic pathway," refers to a series of chemical reactions occurring within a cell, catalyzed by enzymes, to achieve either the formation of a metabolic product, or the initiation of another metabolic pathway. A metabolic pathway may involve several or many steps, and may compete with a different metabolic pathway for specific reaction substrates. Similarly, the product of one metabolic pathway may be a substrate for yet another metabolic pathway.

Metabolic engineering: For the purposes of the present invention, "metabolic engineering" refers to the rational design of strategies to alter one or more metabolic pathways in a cell, such that the step-by-step modification of an initial substance into a product having the exact chemical structure desired is achieved within the overall scheme of the total metabolic pathways operative in the cell.

Desaturase: As used herein, the term "desaturase" refers to a polypeptide that can desaturate (i.e., introduce a double bond) in one or more fatty acids to produce a fatty acid or precursor of interest. Plant-soluble fatty acid desaturase enzymes introduce a double bond regiospecifically into a saturated acyl-ACP substrate. The reaction involves activation of molecular oxygen by a two-electron reduced diiron center coordinated by a four-helix bundle that forms the core of the desaturase architecture. Of particular interest herein are $\Delta^9$ desaturases.

The $\Delta^9$-18:0$^1$-ACP desaturase is required by all plants for the maintenance of membrane fluidity. While this enzyme primarily desaturates stearoyl-ACP, it is also active to a minor extent with palmitoyl-ACP.

Variant desaturase: As used herein, the term "variant desaturase" encompasses those desaturases that exhibit specific activity profiles consistent with a role in producing unusual fatty acids. A variant desaturase may be isolated from an organism, or engineered via a directed evolution program.

Progeny plant: For the purposes of the present invention, "progeny plant," refers to any plant, or plant material obtained therefrom, that may be obtained by plant breeding methods. Plant breeding methods are well-known in the art, and include natural breeding, artificial breeding, selective breeding involving DNA molecular marker analysis, transgenics, and commercial breeding.

Plant material: As used herein, the term "plant material" refers to any cell or tissue obtained from a plant.

Nucleic acid molecule: A polymeric form of nucleotides, which can include both sense and anti-sense strands of RNA, cDNA, genomic DNA, and synthetic forms and mixed polymers of the above. A nucleotide refers to a ribonucleotide, deoxynucleotide, or a modified form of either type of nucleotide. A "nucleic acid molecule" as used herein is synonymous with "nucleic acid" and "polynucleotide." The term includes single- and double-stranded forms of DNA. A nucleic acid molecule can include either or both naturally occurring and modified nucleotides linked together by naturally occurring and/or non-naturally occurring nucleotide linkages.

Nucleic acid molecules can be modified chemically or biochemically, or can contain non-natural or derivatized nucleotide bases, as will be readily appreciated by those of ordinary skill in the art. Such modification include, for example, labels, methylation, substitution of one or more of the naturally occurring nucleotides with an analog, internucleotide modifications, such as uncharged linkages (for example, methyl phosphonates, phosphotriesters, phosphoramidates, carbamates, etc.), charged linkages (for example, phosphorothioates, phosphorodithioates, etc.), pendent moieties (for example, peptides), intercalators (for example, acridine, psoralen, etc.), chelators, alkylators, and modified linkages (for example, alpha anomeric nucleic acids, etc.). The term "nucleic acid molecule" also includes any topological conformation, including single-stranded, double-stranded, partially duplexed, triplexed, hairpinned, circular and padlocked conformations.

Operably linked: A first nucleic acid sequence is operably linked with a second nucleic acid sequence when the first nucleic acid sequence is in a functional relationship with the second nucleic acid sequence. For instance, a promoter is operably linked to a coding sequence if the promoter affects the transcription or expression of the coding sequence. When recombinantly produced, operably linked nucleic acid sequences are generally contiguous and, where necessary to join two protein-coding regions, in the same reading frame. However, nucleic acids need not be contiguous to be operably linked.

Regulatory element: As used herein, the term "regulatory element" refers to a nucleic acid molecule having gene regulatory activity; i.e., one that has the ability to affect the transcription or translation of an operably linked transcribable nucleic acid molecule. Regulatory elements such as promoters, leaders, introns, and transcription termination regions are non-coding nucleic acid molecules having gene regulatory activity which play an integral part in the overall expression of genes in living cells. Isolated regulatory elements that function in plants are therefore useful for modifying plant phenotypes through the techniques of molecular engineering. By "regulatory element," it is intended a series of nucleotides that determines if, when, and at what level a particular gene is expressed. The regulatory DNA sequences specifically interact with regulatory proteins or other proteins.

As used herein, the term "gene regulatory activity" refers to a nucleic acid molecule capable of affecting transcription or translation of an operably linked nucleic acid molecule. An isolated nucleic acid molecule having gene regulatory activity may provide temporal or spatial expression or modulate levels and rates of expression of the operably linked nucleic acid molecule. An isolated nucleic acid molecule having gene regulatory activity may comprise a promoter, intron, leader, or 3' transcriptional termination region.

Promoters: As used herein, the term "promoter" refers to a nucleic acid molecule that is involved in recognition and binding of RNA polymerase II or other proteins such as transcription factors (trans-acting protein factors that regulate transcription) to initiate transcription of an operably linked gene. Promoters may themselves contain sub-elements such as cis-elements or enhancer domains that effect the transcription of operably linked genes. A "plant promoter" is a native or non-native promoter that is functional in plant cells. A plant promoter can be used as a 5' regulatory element for modulating expression of an operably linked gene or genes. Plant promoters may be defined by their temporal, spatial, or developmental expression pattern. The nucleic acid molecules described herein may comprise nucleic acid sequences comprising promoters.

Sequence identity: The similarity between two nucleic acid sequences or between two amino acid sequences is expressed in terms of the level of sequence identity shared between the sequences. Sequence identity is typically expressed in terms of percentage identity; the higher the percentage, the more similar the two sequences. Methods for aligning sequences for comparison are described in detail below.

Analogous position in an amino acid sequence: Nucleic acid and amino acid sequences may be aligned by the methods described in the following paragraphs. When aligned, a position in one sequence is in "an analogous position" with a position in the aligned sequence if the positions are identical within the consensus sequence.

Methods for aligning sequences for comparison are well-known in the art. Various programs and alignment algorithms are described in: Smith and Waterman, Adv. Appl. math. 2:482, 1981; Needleman and Wunsch, J. Mol. Biol. 48:443, 1970; Pearson and Lipman, Proc. Natl. Acad. Sci. USA 85:2444, 1988; Higgins and Sharp, Gene 73:237-44, 1988; Higgins and Sharp, CABIOS 5:151-3, 1989; Corpet et al., Nucleic Acids Research 16:10881-10890, 1988; Huang, et al., Computer Applications in the Biosciences 8:155-65, 1992; Pearson et al., Methods in Molecular Biology 24:307-31, 1994; Tatiana et al., FEMS Microbiol. Lett., 174:247-50, 1990. Altschul et al., J. Mol. Biol. 215:403-10, 1990 (detailed consideration of sequence-alignment methods and homology calculations).

The National Center for Biotechnology Information (NCBI) Basic Local Alignment Search Tool (BLAST) is available on the Internet (at blast.ncbi.nlm.nih.gov/Blast.cgi), for use in connection with sequence-analysis programs, for example, blastp and blastn. A description of how to determine sequence identity using this program is available on the Internet through NCBI at blast.ncbi.nlm.nih.gov/Blast.cgi?CMD=Web&PAGE_TYPE=BlastDocs.

For comparisons of amino acid sequences, the "Blast 2 sequences" function of the BLAST program (bl2seq) is employed using the default parameters. Specific parameters may be adjusted within the discretion of one of skill in the art, to for example, provide a penalty for a mismatch or reward for a match.

Transformed: As used herein, the term "transformed" refers to a cell, tissue, organ, or organism into which has been introduced a foreign nucleic acid molecule, such as a construct. The introduced nucleic acid molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic plant as a parent in, for example, a cross and exhibiting an altered phenotype resulting from the presence of a foreign nucleic acid molecule.

IV. Systematic Metabolic Engineering Approaches to Accumulating Unusual Fatty Acids in a Host Cell, Tissue, or Organism A. Overview An embodiment of the invention includes a systematic approach to metabolic engineering the accumulation of ω-7 fatty acids (FA), comprised of palmitoleic (16:1Δ$^9$) and vaccenic acid (18:1Δ$^{11}$), for example, in plant seeds. To exemplify methods for intercepting the flux of newly synthesized fatty acids in the plastids, Com25, a 16:0-ACP desaturase resulting from a directed evolution program to enhance the 16:0-desaturase activity of the castor Δ$^9$-18:0-desaturase, was expressed under the control of the seed-specific phaseolin promoter. Any seed-specific promoter may be used in the embodiments disclosed herein. This approach increased the accumulation of ω-7 FA from less than 2% in wild type (WT) to about 14% in Com25 transformants.

In further exemplary approaches, expression of Com25 in the fab1/fae1 double mutant, which is impaired in plastidial and extraplastidial fatty acid elongation, respectively, resulted in increased ω-7 FA accumulation to about 50%. Moreover, introducing an additional Com25 under the control of the LTP170 promoter increased 0-7 FA accumulation to about 58%, suggesting that desaturase activity limitation, likely resulting from its low turnover rate, had been overcome. The phaseolin:Com25 construct was expressed in a series of KASII-deficient backgrounds and ω-7 FA content increasing proportionately with 16:0 content up to about 30% with total ω-7 FA accumulation up to about 55% was observed. Interestingly, transgenics accumulating 56% ω-7 FA still contained about 19% 16:0, more than twice that of WT plants. Expression of extraplastidial 16:0 desaturases to intercept the flux of 16:0 en route to triacylglycerol was investigated. Co-expression of plastidial and extraplastidial desaturases along with suppression of KASII in the fab1/fae1 double mutant background resulted in increased accumulation of ω-7 FA from about 2% in WT to about 71% in the best engineered line, equivalent to that found in *Doxantha* seeds.

ω-7 FAs were selected as the target because their synthesis in natural systems, like those of other unusual FA, is initiated by modification of an intermediate of FAS by a variant desaturase enzyme. Cahoon et al., (1997) Plant Mol. Biol. 33:1105-10; and Cahoon et al., (1998) Plant Physiol. 117(2):593-8. In addition, ω-7 FA have potential commercial applications as polymer feedstocks while having similar physical properties to naturally occurring unsaturated fatty acids.

Metabolic engineering studies were initiated by introducing a previously unreported Δ$^9$-16:0-acyl carrier protein (ACP) desaturase, Com25, into the model plant *Arabidopsis* under the control of a seed-specific promoter. Approaches to diverting carbon flow into ω-7 FA by the choice of mutant backgrounds that contain elevated levels of 16:0 and by the co-expression of constructs designed to divert the flux of carbon into the target fatty acid by affecting competition for substrate were explored. Extraplastidial desaturase enzymes were expressed to desaturate residual 16:0 after export from the plastid.

Co-expression of plastidial and extraplastidial desaturases along with suppression of KASII in the fab1/fae1 background resulted in increased accumulation of ω-7 FA to up to about 71% from less than 2% in WT, higher than that found in *Asclepias* and equivalent to that found in *Doxantha* seeds.

16:0-ACP, the precursor of ω-7 fatty acids, is at the first branch point of fatty acid biosynthesis, being competed for by the FatB thioesterase and the KASII elongase; and the introduction of a 16:0-ACP desaturase makes this a three-way competition. Suppression of KASII and FATB are effective ways to reduce competition for substrate and increase the accumulation of ω-7 FA. The increase in ω-7 FA accumulation is saturable at about 30% in the host line, because above this level the desaturase is limiting. Increasing the dosage of Com25 by expressing a second copy under the control of a seed-specific promoter further increased the accumulation of ω-7 fatty acids. However, the seeds of high ω-7 FA accumulators also contained levels of 16:0 in the range of about 20%, presenting an opportunity to desaturate extraplastidial 16:0. Expression of two extraplastidial desaturases increased the accumulation of ω-7 FA, resulting in an approximately 50% decrease of 16:0 in mature seeds.

As described in more detail below, systematic metabolic engineering can be a successful strategy to engineer levels of unusual fatty acid accumulation comparable to those observed in natural sources because the best fab1/fae1/Com25/LnΔ9D and AnΔ9D lines accumulate 71% ω-7 FA, substantially higher levels than in *Asclepias* and equivalent to the levels found in *Doxantha* seeds.

B. Nucleic Acids

Nucleic acid sequences in some embodiments of the present invention show increasing percentage identities when aligned with SEQ ID NO:1. Specific nucleic acid sequences within these and other embodiments may comprise sequences having, for example, at least 60%, 65%, 70%, 75%, 80%, 81%, 82%, 83%, 84%, 85%, 86%, 87%, 88%, 89%, 90%, 91%, 92%, 93%, 94%, 95% 96%, 97%, 98%, or 100% identity with SEQ ID NO:2. It is understood by those of ordinary skill in the art that nucleic acid molecules may be modified without substantially changing the amino acid sequence of an encoded polypeptide, for example, according to permissible nucleotide substitutions according to codon degeneracy.

In some embodiments, nucleic acid molecules of the present invention comprise promoters. Promoters may be selected on the basis of the cell type into which the vector construct will be inserted. Promoters which function in bacteria, yeast, and plants are well-known in the art. The promoters may also be selected on the basis of their regulatory features. Examples of such features include enhancement of transcriptional activity, inducibility, tissue-specificity, and developmental stage-specificity. In plants, promoters that are inducible, of viral or synthetic origin, constitutively active, temporally regulated, and spatially regulated have been described (For example, see Poszkowski, et al., (1989) EMBO J. 3:2719; Odell et al., (1985) Nature 313:810; Chau et al., (1989) Science 244:174-81).

Often used constitutive promoters include, for example, the CaMV 35S promoter, the enhanced CaMV 35S promoter, the Figwort Mosaic Virus promoter, the mannopine synthase promoter, the nopaline synthase promoter, and the octopine synthase promoter.

Useful inducible promoters include, for example, promoters induced by salicylic acid or polyacrylic acids induced by application of safeners (substituted benzenesulfonamide herbicides), heat-shock promoters, a nitrate-inducible promoter derived from the spinach nitrate reductase transcribable nucleic acid molecule sequence, hormone-inducible promoters, and light-inducible promoters associated with the small subunit of RuBP carboxylase and LHCP families.

Examples of useful tissue-specific, developmentally-regulated promoters include the β-conglycinin 7Sα promoter and seed-specific promoters. Plant functional promoters useful for preferential expression in seed plastid include those from proteins involved in fatty acid biosynthesis in oilseeds and from plant storage proteins. Examples of such promoters include the 5' regulatory regions from such transcribable nucleic acid molecule sequences as phaseolin, napin, zein, soybean trypsin inhibitor, ACP, stearoyl-ACP desaturase, and oleosin. Another exemplary tissue-specific promoter is the lectin promoter, which is specific for seed tissue.

Other useful promoters include the nopaline synthase, mannopine synthase, and octopine synthase promoters, which are carried on tumor-inducing plasmids of *Agrobacterium tumefaciens*; the cauliflower mosaic virus (CaMV) 19S and 35S promoters; the enhanced CaMV 35S promoter; the Figwort Mosaic Virus 35S promoter; the light-inducible promoter from the small subunit of ribulose-1,5-bisphosphate carboxylase (ssRUBISCO); the EIF-4A promoter from tobacco (Mandel et al., (1995) Plant Mol. Biol. 29:995-1004); corn sucrose synthetase; corn alcohol dehydrogenase I; corn light harvesting compolex; corn heat shock protein; the chitinase promoter from *Arabidopsis*; the LTP (Lipid Transfer Protein) promoters; *petunia* chalcone isomerase; bean glycine rich protein 1; potato patatin; the ubiquitin promoter; and the actin promoter. Useful promoters are preferably seed-selective, tissue selective, or inducible. Seed-specific regulation is discussed in, for example, EP 0 255 378.

C. Amino Acid Sequences

Amino acid sequences according to some embodiments of the present invention show increasing percentage identities when aligned with SEQ ID NO:2. Specific amino acid sequences within these and other embodiments may comprise sequences having, for example, at least 70%, 75%, 80%, 81%, 82%, 83%, 84%, 85%, 86%, 87%, 88%, 89%, 90%, 91%, 92%, 93%, 94%, 95% 96%, 97%, 98%, or 100% identity with SEQ ID NO:2. In many embodiments, the amino acid sequence having the aforementioned sequence identity when aligned with SEQ ID NO:2 encodes a peptide with enzymatic $\Delta^9$-18:0-ACP desaturase activity.

D. Alteration of Com25: 5 Mutations

Aspects of the present invention concern novel genetically engineered desaturases derived from a parental castor desaturase. In specific embodiments, the genetically engineered desaturase is Com25. Com25 differs from the parental castor desaturase at the following 5 amino acid positions: M114S, T117R, L118C, P179L, and G188T (numbered according to the mature castor desaturase PDB entry 1AFR). In further embodiments, the genetically engineered desaturase may comprise one or more of these 5 mutations in Com25. For example, a genetically engineered desaturase may differ from the parental castor desaturase at the following positions: M114S; T117R; L118C; P179L; G188T; M114S and T117R; M114S and L118C; M114S and P179L; M114S and G188T; T117R and L118C; T117R and P179L; T117R and G188T; L118C and P179L; L118C and G188T; P179L and G188T; M114S, T117R, and L118C; M114S, T117R, and P179L; M114S, T117R, and G188T; M114S, L118C, and P179L; M114S, L118C, and G188T; M114S, P179L, and G188T; T117R, L118C, and P179L; T117R, L118C, and G188T; T117R, P179L, and G188T; or L118C, P179L, and G188T.

E. Hosts Containing Increased Levels of 16:0 Fatty Acids.

In preferred embodiments, host cells or materials transformed with Com25 may exhibit increased levels of 16:0 fatty acids. Host cells may exhibit increased levels of 16:0 fatty acids, for example, by having metabolism of 16:0-ACP reduced in those host cells. Other methods of increasing levels of 16:0 fatty acids in a host cell may be used, and such methods may be chosen by the exercise of the discretion of one of skill in the art. Examples of methods of increasing levels of 16:0 fatty acids in a host cell include, but are not limited to: 1) expression of an extraplastidial desaturase in the host cell; 2) suppression of KASII in the host cell, for example by introducing a mutation in the fab1 gene; and 3) decreasing elongation of 16:0 fatty acids, for example, by introducing a mutation in the fae1 gene.

F. Methods for Genetic Transformation of Plant Material

The present invention is also directed to methods of producing transformed cells which comprise one or more nucleic acid molecules comprising a nucleic acid sequence at least 60% identical to SEQ ID NO: 1. Such nucleic acid molecules may also comprise, for example, non-coding regulatory elements, such as promoters. Other sequences may also be introduced into the cell along with the non-coding regulatory elements and transcribable nucleic acid molecule sequences. These other sequences may include 3' transcriptional terminators, 3' poly-adenylation signals, other untranslated sequences, transit or targeting sequences, selectable markers, enhancers, and operators.

The method of transformation generally comprises the steps of selecting a suitable host cell, transforming the host cell with a recombinant vector, and obtaining the transformed host cell.

Technology for introduction of DNA into cells is well-known to those of skill in the art. These methods can generally be classified into five categories: (1) chemical methods (Graham and Van der Eb (1973) Virology 54(2): 536-9; Zatloukal et al., (1992) Ann. N.Y. Acad. Sci. 660:

136-53); (2) physical methods such as microinjection (Capechi (1980) Cell 22(2):479-88), electroporation (Wong and Neumann, Biochim. Biophys. Res. Commun. (1982) 107(2):584-7; Fromm et al., (1985) Proc. Natl. Acad. Sci. USA 82(17):5824-8; U.S. Pat. No. 5,384,253), and particle acceleration (Johnston and Tang (1994) Methods Cell Biol. 43(A):353-65; Fynan et al., (1993) Proc. Natl. Acad. Sci. USA 90(24):11478-82; (3) viral vectors (Clapp (1993) Clin. Perinatol. 20(1):155-68; Lu et al., (1993) J. Exp. Med. 178(6):2089-96; Eglitis and Anderson (1988) Biotechniques 6(7):608-14); (4) receptor-mediated mechanisms (Curiel et al., (1992) Hum. Gen. Ther. 3(2):147-54; Wagner et al., (1992) Proc. Natl. Acad. Sci. USA 89(13):6099-103); and (5) bacterial-mediated mechanisms, such as with *Agrobacterium*. Alternatively, nucleic acids can be directly introduced into pollen by directly injecting a plant's reproductive organs (Zhou et al., (1983) Methods in Enzymology 101: 433; Hess (1987) Intern. Rev. Cytol. 107:367; Luo et al., (1988) Plant Mol. Biol. Reporter 6:165; Pena et al., (1987) Nature 325:274). Other transformation methods include, for example, protoplast transformation as illustrated in U.S. Pat. No. 5,508,184. The nucleic acid molecules may also be injected into immature embryos (Neuhaus et al., (1987) Theor. Appl. Genet. 75:30).

The most commonly used methods for transformation of plant cells are: the *Agrobacterium*-mediated DNA transfer process (Fraley et al., (1983) Proc. natl. Acad. Sci. USA 80:4803) (as illustrated in U.S. Pat. No. 5,824,877; U.S. Pat. No. 5,591,616; U.S. Pat. No. 5,981,840; and U.S. Pat. No. 6,384,301) and the biolistics or microprojectile bombardment-mediated process (i.e., the gene gun) (such as described in U.S. Pat. No. 5,550,318; U.S. Pat. No. 5,538,880; U.S. Pat. No. 6,160,208; U.S. Pat. No. 6,399,861; and U.S. Pat. No. 6,403,865). Typically, nuclear transformation is desired, but where it is desirable to specifically transform plastids, such as chloroplasts or amyloplasts, plant plastids may be transformed utilizing a microprojectile-mediated delivery of the desired nucleic acid molecule for certain plant species such as *Arabidopsis*, tobacco, potato and *Brassica* species.

*Agrobacterium*-mediated transformation is achieved through the use of a genetically engineered soil bacterium belonging to the genus *Agrobacterium*. Several *Agrobacterium* species mediate the transfer of a specific DNA known as "T-DNA," that can be genetically engineered to carry any desired piece of DNA into many plant species. The major events marking the process of T-DNA mediated pathogensis are: induction of virulence genes, and processing and transfer of TDNA. This process is the subject of many reviews (Ream (1989) Ann. Rev. Phytopathol. 27:583-618; Howard and Citovsky (1990) Bioassays 12:103-8; Kado (1991) Crit. Rev. Plant Sci. 10:1-32; Zambryski (1992) Annual Rev. Plant Physiol. Plant Mol. Biol. 43:465-90; Gelvin (1993) in Transgenic Plants, Kung and Wu eds., Academic Press, San Diego, pp. 49-87; Binns and Howitz (1994) In Bacterial Pathogenesis of Plants and Animals, Dang, ed., Berlin: Springer Verlag., pp. 119-38; Hooykaas and Beijersbergen (1994) Ann. Rev. Phytopathol. 32:157-79; Lessl and Lanka (1994) Cell 77:321-4; Zupan and Zambryski (1995) Annual Rev. Phytopathol. 27:583-618).

To select or score for transformed plant cells regardless of transformation methodology, the DNA introduced into the cell may contain a gene that functions in a regenerable plant tissue to produce a compound that confers upon the plant tissue resistance to an otherwise toxic compound. Genes of interest for use as a selectable, screenable, or scorable marker include, but are not limited to, GUS, green fluorescent protein (GFP), luciferase, and antibiotic or herbicide tolerance genes. Examples of antibiotic resistance genes include genes conferring resistance to the penicillins, kanamycin (and neomycin, G418, bleomycin); methotrexate (and trimethoprim); chloramphenicol; and tetracycline. For example, glyphosate resistance may be conferred by a herbicide resistance gene. Della-Cioppa et al., (1987) Bio/ Technology 5:579-84. Other selection devices can also be implemented including but not limited to tolerance to phosphinothricin, bialaphos, and positive selection mechanisms, Joersbro et al., (1998) Mol. Breed. 4:111-7, and are considered within the scope of the present invention.

The transformed cells, identified by selection or screening and cultured in an appropriate medium that supports regeneration, may then be allowed to mature into plants.

The presently disclosed methods may be used with any transformable plant cell or tissue. Transformable cells and tissues, as used herein, includes but is not limited to those cells or tissues that are capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

The regeneration, development, and cultivation of plants from transformed plant protoplast or explants is known in the art. Weissbach and Weissbach (1988) Methods for Plant Molecular Biology, (Eds.) Academic Press, Inc., San Diego, Calif.; Horsch et al., (1985) Science 227:1229-31. This regeneration and growth process typically includes the steps of selecting transformed cells and culturing those cells through the usual stages of embryonic development through the rooted plantlet stage. Transgenic embryos and seeds are similarly regenerated. In this method, transformants are generally cultured in the presence of a selective media which selects for the successfully transformed cells and induces the regeneration of plant shoots. Fraley et al., (1993) Proc. Natl. Acad. Sci. USA 80:4803. These shoots are typically obtained within two to four months. The resulting transgenic rooted shoots are thereafter planted in an appropriate plant growth medium such as soil. Cells that survive the exposure to a selective agent, or cells that have been scored positive in a screening assay, may be cultured in media that supports regeneration of plants. The shoots may then be transferred to an appropriate root-inducing medium containing the selective agent and an antibiotic to prevent bacterial growth. Many of the shoots will develop roots. These are then transplanted to soil or other media to allow the continued development of roots. The method, as outlined above, will generally vary depending on the particular plant strain employed, and particulars of the methodology are therefore within the discretion of one of skill in the art.

The regenerated transgenic plants may be self-pollinated to provide homozygous transgenic plants. Alternatively, pollen obtained from the regenerated transgenic plants may be crossed with non-transgenic plants, preferably inbred lines of agronomically important species. Conversely, pollen from non-transgenic plants may be used to pollinate the regenerated transgenic plants.

The transgenic plant may pass along the transformed nucleic acid sequence to its progeny. The transgenic plant is preferably homozygous for the transformed nucleic acid sequence and transmits that sequence to all of its offspring upon, and as a result of, sexual reproduction. Progeny may be grown from seeds produced by the transgenic plant. These additional plants may then be self-pollinated to generate a true breeding line of plants.

The progeny from these plants may be evaluated, among other things, for gene expression. The gene expression may be detected by several common methods such as western blotting, northern blotting, immunoprecipitation, and ELISA (Enzyme-Linked ImmunoSorbent Assay). The transformed plants may also be analyzed for the presence of the introduced DNA and the expression level and/or fatty acid profile conferred by the nucleic acid molecules and amino acid molecules of the present invention. Those of skill in the art are aware of the numerous methods available for the analysis of transformed plants. For example, methods for plant analysis include, but are not limited to, Southern blots or northern blots, PCR-based approaches, biochemical assays, phenotypic screening methods, field evaluations, and immunodiagnostic assays.

Methods for specifically transforming dicots are well-known to those skilled in the art. Transformation and plant regeneration using these methods have been described for a number of crops including, but not limited to, members of the genus *Arabidopsis*, cotton (*Gossypium hirsutum*), soybean (*Glycine max*), peanut (*Arachis hypogaea*), and members of the genus *Brassica*. Methods for transforming dicots, primarily by use of *Agrobacterium tumefaciens* and obtaining transgenic plants have been published for cotton (U.S. Pat. No. 5,004,863; U.S. Pat. No. 5,159,135; U.S. Pat. No. 5,518,908); soybean (U.S. Pat. No. 5,569,834; U.S. Pat. No. 5,416,011; McCabe, et al., (1988) Biotechnology 6:923; Christou et al., (1988) Plant Physiol. 87:671-4; *Brassica* (U.S. Pat. No. 5,463,174); peanut (Cheng et al., (1996) Plant Cell Rep. 15:653-7; McKently et al., (1995) Plant Cell Rep. 14:699-703; papaya; and pea (Grant et al., (1995) Plant Cell Rep. 15:254-8).

Methods for transforming monocots are also well-known in the art. Transformation and plant regeneration using these methods have been described for a number of crops including, but not limited to, barley (*Hordeum vulgarae*); maize (*Zea mays*); oats (*Avena sativa*); orchard grass (*Dactylis glomerata*); rice (*Oryza sativa*, including indica and japonica varieties); sorghum (*Sorghum bicolor*); sugar cane (*Saccharum* sp); tall fescue (*Festuca arundinacea*); turf-grass species (e.g., *Agrostis stolonifera, Poa pratensis, Stenotaphrum secundatum*); wheat (*Triticum aestivum*); and alfalfa (*Medicago sativa*). It is apparent to those of skill in the art that a number of transformation methodologies can be used and modified for production of stable transgenic plants for any number of target crops of interest.

Any plant may be chosen for use in the presently disclosed methods. Preferred plants for modification according to the present invention include *Arabidopsis thaliana*, borage (*Borago* spp.), Canola, castor (*Ricinus communis*), cocoa bean (*Theobroma cacao*), corn (*Zea mays*), cotton (*Gossypium* spp), *Crambe* spp., *Cuphea* spp., flax (*Linum* spp.), *Lesquerella* and *Limnanthes* spp., Linola, nasturtium (*Tropaeolum* spp.), *Oenothera* spp., olive (*Olea* spp.), palm (*Elaeis* spp.), peanut (*Arachis* spp.), rapeseed, safflower (*Carthamus* spp.), soybean (*Glycine* and *Soja* spp.), sunflower (*Helianthus* spp.), tobacco (*Nicotiana* spp.), *Vernonia* spp., wheat (*Triticum* spp.), barley (*Hordeum* spp.), rice (*Oryza* spp.), oat (*Avena* spp.) sorghum (*Sorghum* spp.), rye (*Secale* spp.) or other members of the Gramineae.

It is apparent to those of skill in the art that a number of transformation methodologies can be used and modified for production of stable transgenic plants from any number of target crops of interest.

G. Transgenic Seeds

In some embodiments of the invention, a transgenic seed comprises a polypeptide comprising an amino acid sequence at least 90% identical to SEQ ID NO:2. In these and other embodiments, the transgenic seed comprises a nucleic acid sequence at least 60% identical to SEQ ID NO: 1. In certain embodiments, the seeds of the present invention exhibit increased levels of unusual fatty acids, for example, ω-7 fatty acids, such as $16:1\Delta^{19}$ and/or $18:1\Delta^{11}$. The seeds can be harvested from fertile transgenic plants and be used to grow progeny generations of transformed plants of this invention, including hybrid plant lines comprising a nucleic acid sequence according to this invention and another gene or nucleic acid construct of interest.

Each document, patent, and reference cited herein is herein incorporated by its entirety.

The following examples are provided to illustrate certain particular features and/or embodiments. These examples should not be construed to limit the invention to the particular features or embodiments described.

EXAMPLES

Example I: Materials and Methods

Plant Growth and Transformation

*Arabidopsis* plants were grown in soil under continuous exposure to 300 microeinsteins of light (1 microeinstein=1 mol of light) in E7/2™ controlled environment growth chambers (Conviron). The plants were transformed according to Clough and Bent's method, Clough and Bent (1998) Plant J. 16(6):735-43, using *Agrobacterium tumefaciens* strain GV3101. We identified individual $T_1$ seeds carrying the transgenes by the fluorescence emitted, Stuitje et al., (2003) Plant Biotechnol. J. 1(4):301-9, upon illumination with green light from an X5 LED™ flashlight (Inova) in conjunction with a 25A red camera filter. Pidkowich et al., (2007) Proc. Natl. Acad. Sci. USA 104(11): 4742-7. A WILD™ M3Z dissection microscope equipped with an Olympus U-LH100HG™ illumination system was used to discriminate between seeds carrying Zs-Green and Ds-Red markers with the use of filters FITC 535 and FITC 515, respectively. Seed-specific expression was achieved by placing constructs under the control of the phaseolin seed-storage protein promoter or the LTP170 promoter. Slightom et al., (1983) Proc. Natl. Acad. Sci. USA 80(7):1897-1901; and van der Geest and Hall (1997) Plant Mol Biol. 33(3): 553-7.

Source of Com25

Figure 5:
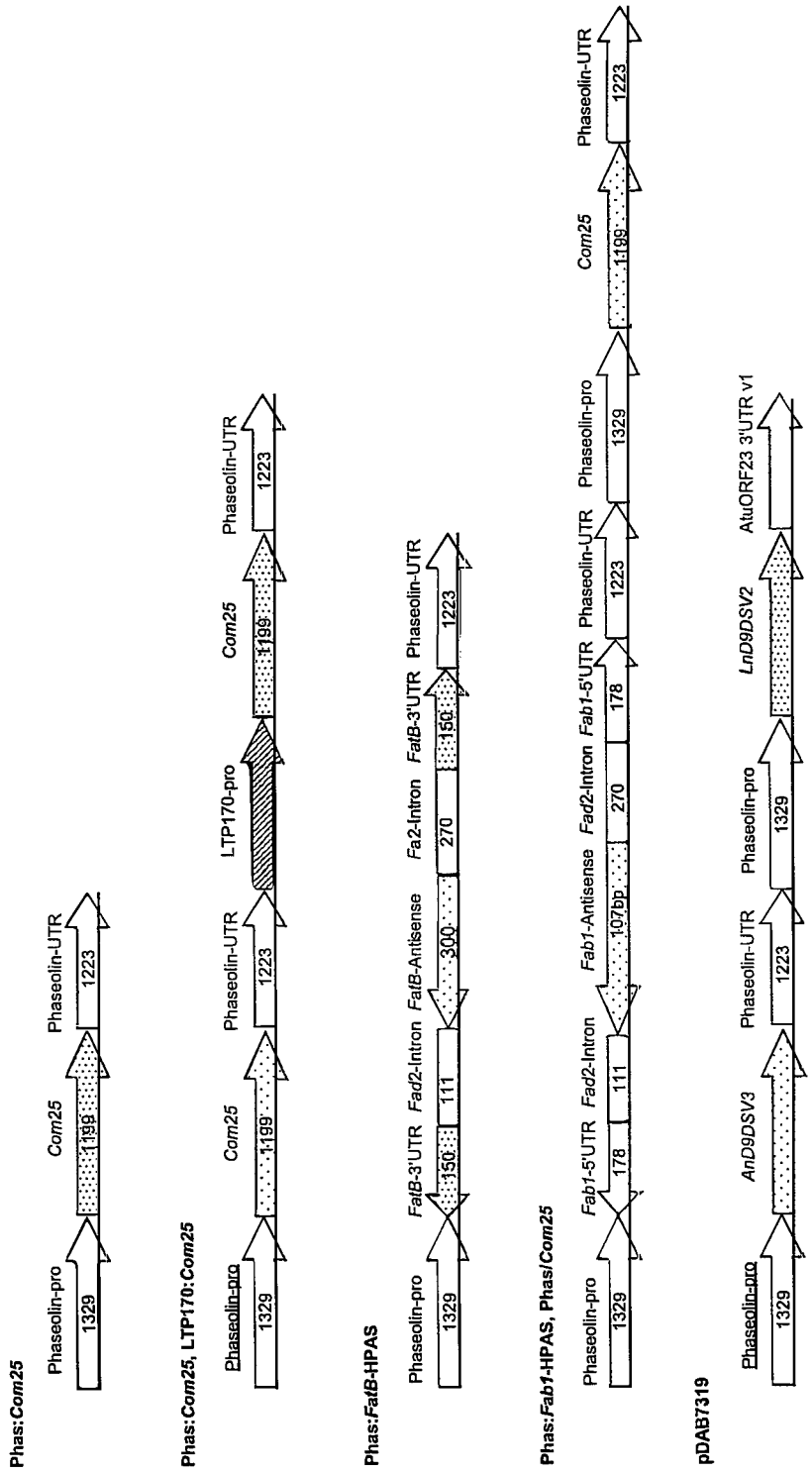
FIG. 5. is a schematic arrangement of DNA elements in particular construct embodiments of the invention.

Com25 is a variant of the *Ricinus communis* $\Delta^9$-18:0-ACP desaturase that arose from a program of combinatorial saturation mutagenesis/selection designed to identify variants with improved activity towards acyl chains of less than 18C in lengths. Whittle and Shanklin (2001) J. Biol. Chem. 276(24):21500-5. Com25 differs from the parental castor desaturase at the following 5 amino acid positions: M114S, T117R, L118C, P179L, and G188T (numbered according to the mature castor desaturase PDB entry 1AFR).

Plasmid Constructs

Phas:Com25. The entire open reading frame of the castor variant Com25, engineered to contain its authentic transit peptide and flanked by 5' PacI and 3' XhoI restriction sites was cloned into the corresponding sites of plasmid pDs- Red-Phas, Pidkowich et al., (2007) Proc. Natl. Acad. Sci. USA 104(11): 4742-7, (with Ds-Red marker) to create Phas:Com25 (FIG. 5).

Phas:Com25, LTP170:Com25. The LTP170 promoter was amplified from *Arabidopsis* genomic DNA using primers P17-5'BamHI (GGGATCCCCGGGTTGACATTTTTA CCTTTTT; SEQ ID NO:3) and P17-3'PacI (GGTTAAT- TAAGTCTTCAAACTCTAGGA; SEQ ID NO:4), subcloned into pGEMT-Easy before isolation of the BamHI- PacI fragment, which was cloned into the corresponding sites of plasmid pDs-Red-Phas:Com25 (described, supra) to create pDs-Red-LTP170:Com25. A fragment containing Com25 along with the phaseolin terminator was excised using BamHI and EcoRV and cloned into the BamHI and SmaI restriction sites within vector pDs-Red-LTP170- Com25 to create Phas:Com25/LTP170:Com25 (FIG. 5).

Phas:Fab1-HPAS. This construct was created in two steps; first the construction of Phas:FatB-HP, and afterwards the insertion of an antisense portion of the FatB gene to replace part of the Fad2 intron separating the sense and antisense portions of the FatB gene comprising the hairpin. To achieve this, 150 bp of the *Arabidopsis* FatB 3'UTR was amplified from genomic DNA in both sense (using primers FatB-hps-5'PstI GGGCTGCAGAAACAAGTTTCGGC- CACCAACC C; SEQ ID NO:5 and FatB-hps-3'XhoI CCCCTCGAGACATCAGAATTCGTAATGAT; SEQ ID NO:6) and antisense (using primers FatB-hpa-5'NheI GGGGCTAGCAAGTTTCGGCCACCAAC CC; SEQ ID NO:7 and FatB-hpa-3'PacI CCCTTAATTAAACATCA- GAATTCGTAATGAT; SEQ ID NO:8) orientations. These fragments were restricted with PstI/XhoI and NheI/PacI and used to replace the 5'UTR sense and antisense portions of FabI in pGEM-T-Easy-HTM3, Pidkowich et al., (2007) Proc. Natl. Acad. Sci. USA 104(11): 4742-7, at their equivalent sites, to create the intermediate plasmid pGEM-T-Easy- HTM4. To create a 300 bp antisense portion of the FatB coding region, a fragment was amplified with primers FatB- Exon-5'Sp-Bam (CCACTAGTGGATCCACCTCTGC- TACGTCGTCATT; SEQ ID NO:9) and FatB-Exon-3'Bg- Sal (GGAGATCTGTCGACGTAGTTATAGCAGCAAGA AG; SEQ ID NO:10), and the fragment, restricted with BamHI and SalI, was used to replace part of the Fad2-intron after restriction with BglII and SpeI to create pGEM-T-Easy- HTM5.

The assembled HPAS fragment was excised with the use of PacI and XhoI and cloned into the equivalent sites of pZs-Green-Phas:Com25 (plasmid pDs-Red-Phas:Com25, described, supra, in which the fluorescence marker pCVMV: Ds-Red had been replaced by a green fluorescent protein marker pCVMV:Zs-Green™ (Clonetech)) to create plasmid Phas:FatB-HPAS (FIG. 5).

Phas:AnD9d, Phas:LnD9D. Two fungal acyl-CoA D9 desaturases were combined in plasmid pDAB7318 with both genes being driven by the seed-specific Phas promoter from *Phaseolus vulgaris*. The first gene in the construct was an acyl-CoA Δ9-desaturase from *Aspergillus nidulans* that was redesigned and synthesized for optimal expression in plants (US Patent Application 20080260933A1) and fused to the 3' untranslated region and 3' MAR from the *Phaseolus vulgaris* phaseolin gene. The second desaturase gene in this construct was an acyl-CoA Δ9-desaturase from *Leptosphaeria nodorum* that was also redesigned and synthesized for plant expression and fused to the *Agrobacterium tumefaciens* ORF23 3' untranslated region. This desaturase was identified by homology searches of the *S. nodorum* genome sequence released by the *Leptosphaeria nodorum* Sequencing Project, Broad Institute of Harvard and MIT (http://www.broad.mit- .edu). It was shown to have a preference for desaturation of palmitate by complementation of the ole1 mutant of *Saccharomyces cerevisiae*. Phas:Fab1-HPAS-Phas:Com25. To simplify gene stacking experiments, plasmid Phas:Fab1/ HPAS-Phas:Com25 was constructed to combine Com25 expression with KASII suppression. To achieve this, the Phaseolin terminator was isolated from Phas:Com25 and cloned into the intermediate vector pBL, with the EcoRV- EcoRV fragment containing the Phaseolin promoter driving Com25, to create pBL-Phas:Com25-PhasTer. This Com25 expression cassette was excised using flanking EcoRI- EcoRI restriction sites and cloned into the corresponding site within Phas:Fab1-HPAS to create Phas:Fab1-HPAS-Phas- Com25. See FIG. 5.

Fatty-Acid Analysis

To analyze the fatty acids of single seeds, fatty-acid methyl esters (FAMEs) were prepared by incubating the seeds with 0.2M trimethylsulfonium hydroxide in methanol. Butte et al., (1982) Anal. Lett. 15(10):841-50. To similarly analyze bulk seeds, FAMEs were prepared by incubating the seeds in 0.5 mL $BCl_3$ for 1 h at 80° C., extracting them with 1 mL hexane, and then drying under $N_2$. FAMEs were analyzed either with an HP6890™ gas chromatograph-flame ionization detector (Agilent Technologies), or an HP5890™ gas chromatograph-mass spectrometer (Hewlett-Packard) fitted with 60-m×250-µM SP-2390 capillary columns (Supelco). The oven temperature was raised during the analyses from 100° C. to 240° C. at a rate of 15° C./min with a flow rate of 1.1 mL/min. Mass spectrometry was performed with an HP5973™ mass selective detector (Hewlett-Packard). We determined the double-bond positions of monounsaturated FAMEs by dimethyl sulfide derivatization. Yamamoto et al., (1991) Chem. and Phys. Lipids 60(1):39-50.

Example II: Expression of Com25 in WT *Arabidopsis*

Several plants including *Asclepias*, Hopkins and Chisholm (1961) Can. J. Biochem. Physiol. 39:829-35, and *Doxantha*, Chisholm and Hopkins (1965) J. Am. Oil Chem. Soc. 42:49-50, have been reported to accumulate ω-7 FA in their seeds. Genes encoding the desaturase enzymes responsible for synthesizing palmitoleate have been isolated. The activities of the corresponding recombinant desaturase enzymes, Cahoon et al., (1997) Plant Mol. Biol. 33:1105-10; Cahoon et al., (1998) Plant Physiol. 117(2):593-8, were, like those for many variant desaturases, lower than those reported for archetypal stearoyl-ACP desaturases. Whittle and Shanklin (2001) J. Biol. Chem. 276(24):21500-5. We compared the effects of expressing the *Asclepias* and *Doxantha* desaturases and several variants of the castor desaturase, including the desaturase from castor variety 5.2 and Com25 that arose from directed evolution experiments designed to enhance the 16:0-desaturase activity of the castor $\Delta^9$-18:0-desaturase, Whittle and Shanklin (2001) J. Biol. Chem. 276(24):21500- 5, in *Arabidopsis*. In these experiments, Com25 outperformed the other desaturase enzymes, Bondaruk et al., (2007) Plant Breeding 126:186-94, increasing the accumulation of $16:1\Delta^9$ and its elongation product, $18:1\Delta^{11}$ in WT *Arabidopsis* from barely detectable levels in untransformed plants to about 2% and about 12% respectively; yielding a total of about 14% ω-7 fatty acids in Com25 transformants. FIG. 2A; FIG. 2B.

Table 1 shows that while Com25 has a much improved $k_{cat}$ (11.1 min$^{-1}$) over castor WT (2.8 min$^{-1}$) for 16:0-ACP substrate, it falls short of that reported for castor variant 5.2 (25.3 min$^{-1}$). Whittle and Shanklin (2001) J. Biol. Chem.

276(24):21500-5. However, Com25's $K_m$ for 16:0-ACP (0.12 μM) is 4.6-times lower than that of castor variant 5.2 (0.55) and 42-times lower than that of castor WT (5.0). The resulting specificity factor with 16:0-ACP substrate for com25 of 91 $\mu M^{-1} \cdot min^{-1}$ is approximately twice that of castor variant 5.2 and 163-times that of castor WT. Indeed, Com25's specificity factor with 16:0-ACP is equivalent to that of castor WT with its natural 18:0-ACP substrate (92 $\mu M^{-1} \cdot min^{-1}$). Com25's improved $K_m$ for 16:0-ACP relative to castor variant 5.2 suggests it completes more effectively with FatB and KASII for substrate, providing an explanation as to why its expression facilitates greater accumulation of ω-7 FA than castor variant 5.2, despite its lower $K_{cat}$.

Kinetic parameters of castor desaturase and its variants with various substrates.

TABLE 1

| Enzyme $min^{-1b}$ | Substrate μM | $k_{cat}$ $\mu M^{-1} \cdot min^{-1}$ | $K_m$ | specificity factor $k_{cat}/K_m$ |
|---|---|---|---|---|
| com25 | 16:0-ACP | 11.1 (0.6) | 0.12 (0.03) | 91 |
| 5.2 | 16:0-ACP | 25.3 (1.1) | 0.55 (.06) | 46 |
| WT | 16:0-ACP | 2.8 (0.1) | 5.0 (0.5) | 0.56 |
| WT | 18:0-ACP | 42.3 (1.6) | 0.46 (0.05) | 92 |

Example IV: Expression of Com25 in Hosts Containing Increased Levels of 16:0

In WT *Arabidopsis*, fatty acids are synthesized de novo via the ACP track to a first branch point at the level of 16:0-ACP. FIG. 1. If acted on by FATB, the palmitoyl thioesterase, 16:0 free fatty acid is released from the plastid to the cytoplasm where it is esterified to CoA, and subsequently transesterified onto phospholipids of the endomembrane system. Alternatively, β-ketoacyl-ACP synthase II (KASII) elongates the majority of 16:0-ACP to 18:0-ACP whereupon it is desaturated by the $\Delta^9$-stearoyl-ACP desaturase to produce oleoyl-ACP. FATA, the oleoyl-ACP thioesterase releases the oleic acid, which exits the plastid and, like the palmitate, becomes activated to the CoA-thioester and is transferred to the phospholipids. In the ER, oleate can be elongated to $10:1\Delta^{11}$ via the action of the fatty acid elongase (FAE) I, or become sequentially desaturated by the action of FAD2 and FAD3 to produce linolenic or linolenic acids respectively.

16:0-ACP is the earliest metabolite in the FA synthesis pathway that can be committed to ω-7 production by its desaturation to $16:1\Delta^9$-ACP. To achieve this, the feasibility of expressing a plastidial $\Delta^9$-16:0-ACP-specific desaturase under the control of a seed-specific promoter was explored (see FIG. 1 (reaction 1)).

Figure 2:
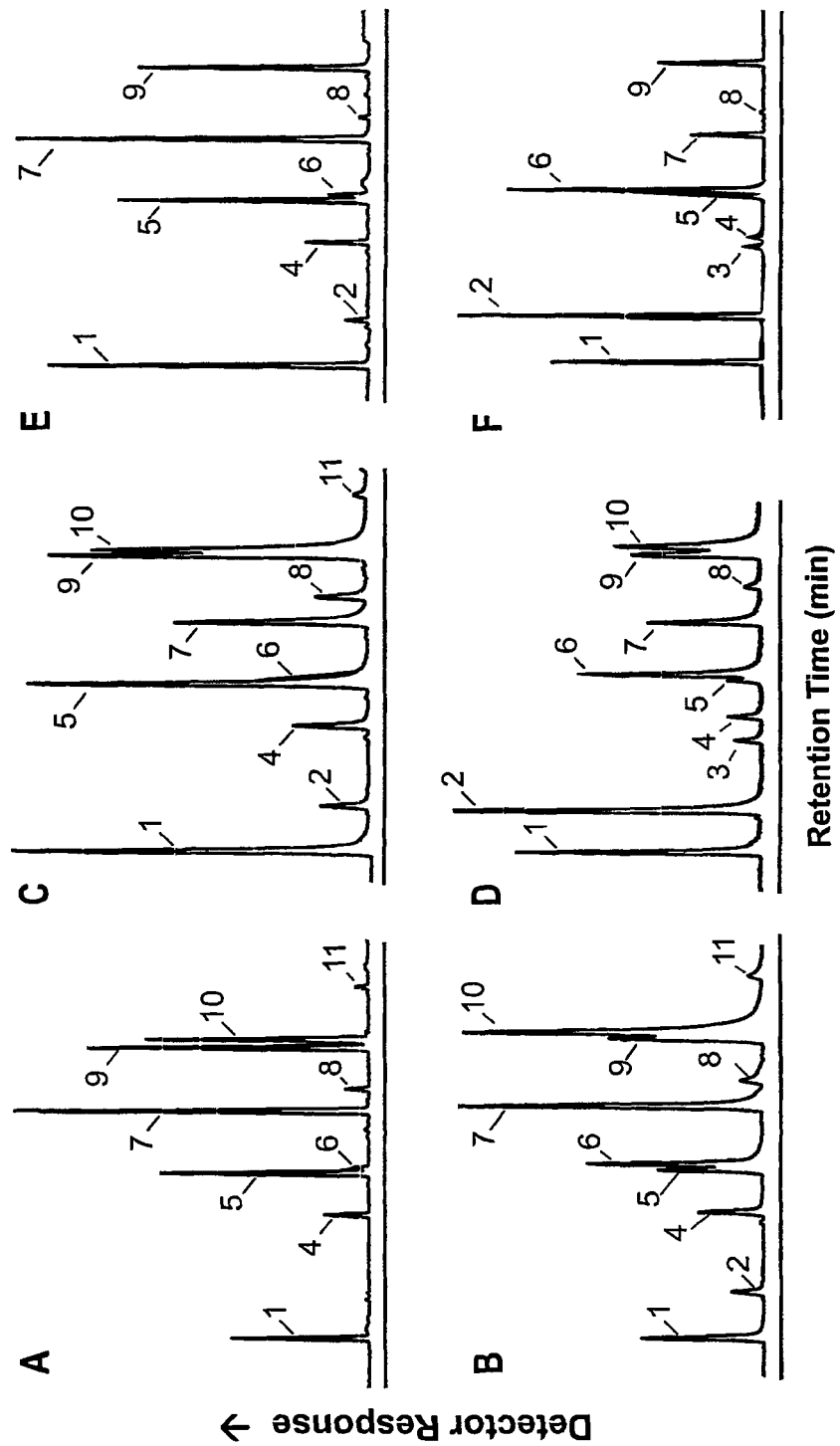
FIG. 2 displays a representative gas chromatographic separation of FAMEs upon expression of Com25 in various backgrounds of *Arabidopsis*. Panels A and B, WT; C and D, fab1; E and F, fab1/fae1. Panels A, C and E, untransformed; B, D and F, transformed with Phas:Com25. FAME peaks are indicated: 16:0 (1), 16:1Δ$^9$ (2), 16:2 (3), 18:0 (4), 18:1 Δ$^9$ (5), 18:1Δ$^{11}$ (6), 18:2 (7), 20:0 (8), 20:1Δ$^{11}$ (6), 18:2 (7), 20:0 (8), 20:1Δ$^{11}$ (9), 18:3+20:1Δ$^{13}$ (10), and 22:1 (11).

As described, supra, P3-ketoacyl-ACP synthase II (KAS II) elongates 16:0-ACP to 18:0-ACP. Therefore, lines with lowered KASII activity were sought that would contain increased levels of 16:0 substrate. FIG. 2 shows representative GC traces of seed FA methyl esters. Despite many mutagenesis screens, only one mutant fab1 has been reported, James and Dooner (1990) Theor. Apple Genet. 80:241-45, that exhibits increased 16:0 levels in leaves and seeds, which contain about 21% of 16:0 compared to about 10% in WT, as shown in FIG. 2C; and Table 2. Biochemical evidence showed that the fab1 lesion is in KASII, because its activity was reduced in the mutant. Carlsson et al., (2002) Plant J. 29(6):761-70. Expression of Com25 in fab1 increased the accumulation of $16:1\Delta^9$ and $18:1\Delta^{11}$ to about 23% and about 16% respectively, yielding a total of about 39% ω-7 FA. FIG. 2D; and Table 2. This large increase of ω-7 FA upon the expression of Com25 in the fab1-1 background correlates with the increase in total 16:0 accumulation in mature seeds and likely results from decreased competition for 16:0-ACP substrate by KASII.

We also combined the fab1 mutation with fae1, because its deficiency in extraplastidial elongation of C18 to C20 fatty acids further increases the amount of 16:0 fatty acids, and simplifies analysis. The untransformed double mutant contains about 9% of ω-7 fatty acids, presumably reflecting increased desaturation of 16:0-ACP by the $\Delta^9$-18:0-ACP desaturase in the presence of increased levels of 16:0-ACP substrate. FIG. 2E; and Table 2. Expression of Com25 in fab1/fae1 resulted in an increase of $16:1\Delta^9$ and $18:1\Delta^{11}$ to about 26% and about 23% respectively, yielding an increase of ω-7 FA to about 50%. FIG. 2F; and Table 2.

Figure 3:
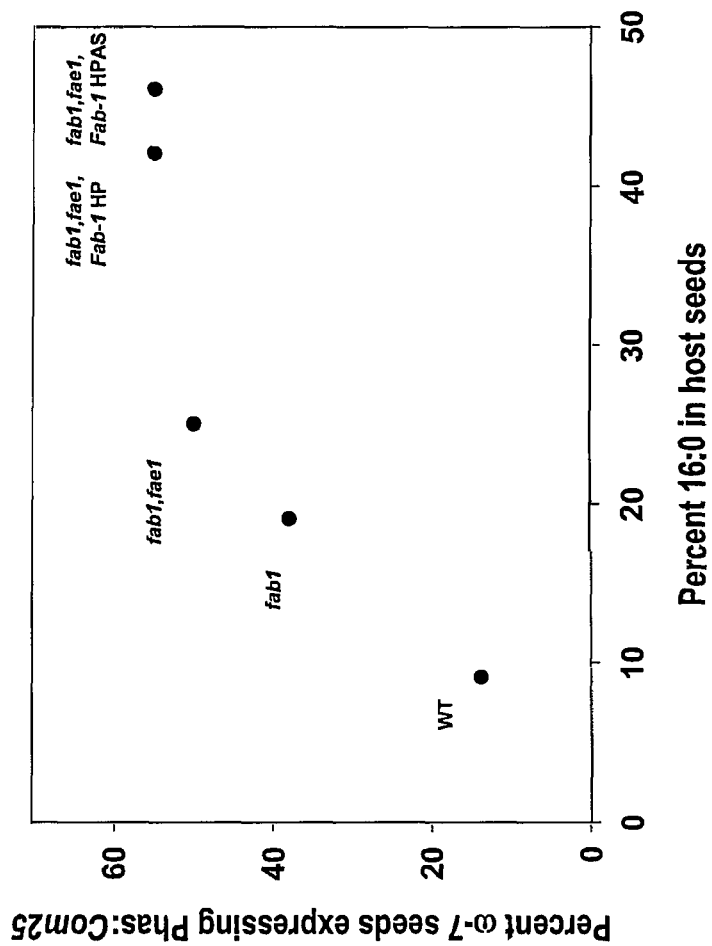
FIG. 3 shows the relationship between 16:0 in host seeds versus ω-7 accumulation (as mol percent).
Figure 4:
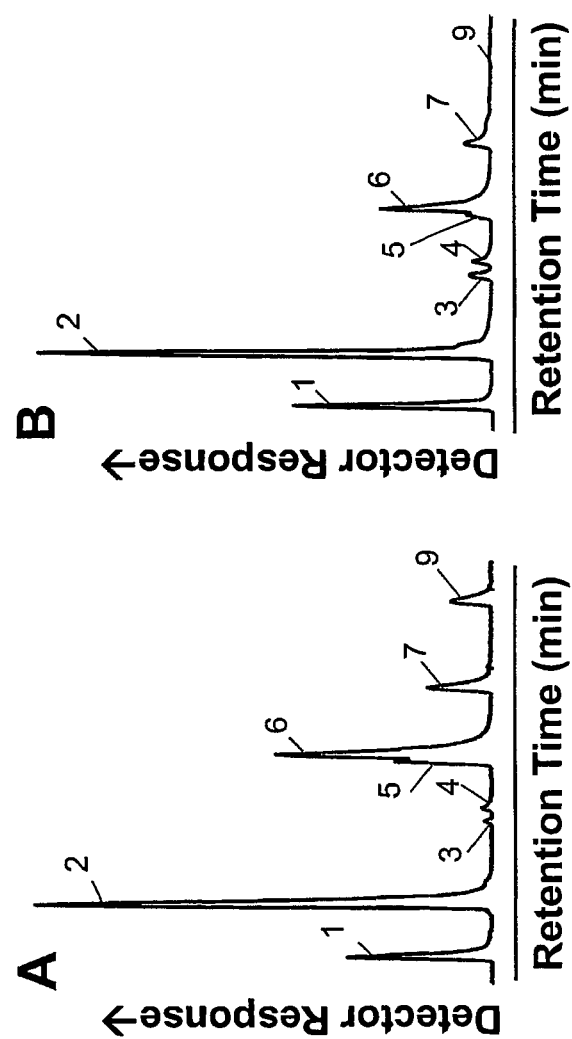
FIG. 4 displays a representative gas chromatographic separation of FAMEs upon expression of Com25 in various backgrounds or *Arabidopsis*. Panel A: best fab1/fae1, Phas:Com25, Fab1-HPAS, AnΔ9DS, LnΔ9DS transformant line; Panel B: *Doxantha* seed. Peak designations are as described in FIG. 2.

From the above results, increased accumulation of 16:1 in fab1 and fab1/fae1 seeds correlates with increased 16:0, and so we sought lines to express Com25 in which 16:0 levels were higher than that of the fab1/fae1 double mutant. Two such mutants were recently reported in which Fab1 was suppressed, one by hairpin (HP)RNAi, Pidkowich et al., (2007) Proc. Natl. Acad. Sci. USA 104(11): 4742-7, and the other by a novel method of suppression termed hairpin-antisense (HPAS)RNAi, Nguyen and Shanklin (2009) Journal of the American Oil Chemists Society 86:41-9. These lines contain strongly elevated seed 16:0 accumulation levels at 42% and 46%, respectively. FIG. 3. Transformation with Com25 yielded a further increase of about 5% of ω-7 FA in both cases. Table 2. Thus, increases in 16:0 accumulation at low levels of 16:0 is predictive of increased Com25 desaturation as evidenced by proportional increases in ω-7 FA accumulation, but this response is apparently saturable at a little over 30%, as there was no difference between ω-7 FA accumulation expression in hosts accumulating either 42% or 46% 16:0. FIG. 3. Without intending to be bound by any particular theory, it is possible that factors other than substrate, i.e., desaturase abundance and/or availability of reductant become limiting in these transgenics.

Recently, a T-DNA knockout allele, fab1-2 was described that has increased 16:0 levels in the heterozygote; however, the homozygote was shown to be embryo lethal. Pidkowich et al., (2007) Proc. Natl. Acad. Sci. USA 104(11): 4742-7. We hypothesized that the lethal phenotype results from the reduction of unsaturated fatty acids, and theorize that expression of Com25 in this line may confer viability. In contrast, the fab1/fae1 double mutant is viable in the homozygous condition and is indistinguishable in growth and development from WT. We therefore used the fab1/fae1 double mutant as an experimental host for subsequent experiments.

Example V: Increasing Com25 Gene Dosage Results in Increased ω-7 Accumulation The archetypal castor $\Delta^9$-18:0-ACP desaturase has a $k_{cat}$ of 42 min$^{-1}$, Whittle and Shanklin (2001) J. Biol. Chem. 276(24):21500-5; which is several-fold higher than those reported for $\Delta^9$-16:0-ACP desaturases. Cahoon et al., (1997) Plant Mol. Biol. 33:1105-10; and Cahoon et al., (1998) Plant Physiol. 117(2):593-8. While this turnover is comparable to those of similar Fe-dependent oxidation reactions such as cytochrome P450s, these rates are lower (in many cases, by orders of magnitude) than many metabolic enzymes. The low turnover rates of desaturases necessitate high levels of protein expression in order to account for the desaturation of a large proportion of the carbon stored in the seed, raising the possibility that the abundance of desaturase enzyme might limit ω-7 accumulation. To test this hypothesis, Com25 was engineered under the control of a seed-specific LTP170 promoter (that controls the expression of a seed storage protein) and co-expressed this along with the phaseolin-driven Com25 construct described above. Co-expression of Com25 under the control of the phaseolin and LTP170 promoters in the fab1/fae1 background resulted in an increase of ω-7 FA accumulation from about 50% to about 58%; the increase in the 16:1 $\Delta^9$ being larger (about 6%) than that of 18:1 $\Delta^{11}$ (about 2%). This increase in ω-7 FA accumulation is moderate suggesting that Com25 is likely not limiting in seeds expressing both Com25 constructs.

Example VI: Expression of Extraplastidial Δ9-16:0 Desaturases Increases ω-7 FA Accumulation As previously discussed, the use of background Arabidopsis that accumulates high levels of 16:0 correlates with the formation of ω-7 FA upon expression of a 16:0-ACP desaturase, but much of the 16:0 still leaves the plastid and accumulates in the seed oil. See Table 2. Therefore, two approaches to reduce the accumulation of this 16:0 in seed oil were considered. One strategy was to reduce the activity of the palmitate thioesterase FATB (FIG. 1) that cleaves 16:0 from 16:0-ACP. Suppression of FATB via HPAS-RNAi reduced 16:0 accumulation by about 3%, with about a 6% increase of the ω-7 FA. See Table 2. The feasibility of further reducing the accumulation of seed 16:0 beyond what was observed by suppression of FATB by desaturating the 16:0 after export from the plastid was explored.

Free fatty acids released from the plastid become esterified to CoA by acyl Co-A synthases en route to accumulation as triacylglycerols. Shockey et al., (2003) Plant Physiol. 132(2):1065-76. These cytoplasmic fatty acyl Co-As and phospholipid-linked FA represent pools of substrates potentially available for extraplastidial desaturases. The expression of extraplastidial fungal Aspergillus nidulans (An) and Leptosphaeria nodurum (Ln) desaturases, either alone or in combination, were evaluated with respect to reducing 16:0 levels in Arabidopsis. Co-expression of two desaturases from Ln and An under the control of the phaseolin promoter yielded promising results in reducing 16:0 in WT Arabidopsis. Therefore, the expression of the Ln and An construct along with the expression of a single copy of Com25 in a KASII HPAS-RNAi suppression line was tested. Expression of LnΔ9D and AnΔ9 desaturases resulted in the conversion of approximately half of the 16:0 to 16:1$\Delta^9$, resulting in a decrease in 16:0 accumulation in seeds from about 19% to about 11% (approximately the level seen in WT seeds), with a corresponding increase in 16:1$\Delta^9$ from about 27% to 43%.

TABLE 2

| Plant | % Fatty Acid | | | | | | | | | | | |
|---|---|---|---|---|---|---|---|---|---|---|---|---|
| | 16:0 | 16:1Δ9 | 16:2 | 18:0 | 18:1Δ9 | 18:1Δ11 | 18:2 | 18:3 | 20:0 | 20:1 | Tot ω-7 | Δ |
| WT | 10.4 ± 0.4 | 0.1 ± 0.06 | 0 | 3.7 ± 0.4 | 14.5 ± 2.2 | 1.7 ± 0.2 | 26.6 ± 0.9 | 20.2 ± 1.1 | 2.1 ± 0.3 | 20.7 ± 0.6 | 1.8 ± 0.2 | — |
| fab1 | 20.8 ± 1.6 | 1.5 ± 0.5 | 0 | 3.7 ± 0.4 | 18.4 ± 1.3 | 2.8 ± 0.9 | 14.8 ± 2.7 | 19.1 ± 1.3 | 3.1 ± 0.8 | 15.8 ± 1.0 | 4.3 ± 1.3 | 2 |
| fab1, fae1 | 26.8 ± 1.9 | 1.9 ± 0.3 | 0 | 3.6 ± 0.5 | 15.8 ± 1.5 | 6.8 ± 0.8 | 25.3 ± 2.5 | 19.7 ± 1.5 | 0.2 ± 0.1 | 0 | 8.7 ± 1.1 | 4 |
| WT, Com25 | 9.2 ± 1.5 | 1.6 ± 0.4 | 0 | 3.7 ± 0.3 | 5.7 ± 1.6 | 12.8 ± 1.2 | 26.6 ± 1.6 | 29.6 ± 2.2 | 2.1 ± 0.4 | 8.7 ± 2.1 | 14.4 ± 1.5 | 12 |
| fab1 Com25 | 18.6 ± 2.1 | 23.5 ± 3.7 | 1.6 ± 0.5 | 1.9 ± 0.3 | 2.9 ± 2.2 | 15.6 ± 3.3 | 9.6 ± 1.7 | 17.1 ± 1.8 | 1.0 ± 0.4 | 8.2 ± 3.4 | 39.1 ± 1.9 | 35 |
| fab1, fae1 Com25 | 22 ± 2.6 | 26.2 ± 2.9 | 2.0 ± 0.4 | 1.8 ± 0.4 | 3.7 ± 1.1 | 23.4 ± 2.3 | 8.6 ± 0.7 | 12.4 ± 1.8 | 0 | 0 | 49.6 ± 1.1 | 41 |
| fab1, fae1 com25 Fab1-HPA S | 20.7 ± 2.1 | 30.3 ± 1.6 | 2.2 ± 0.2 | 0.9 ± 0.6 | 4.7 ± 1.4 | 24.5 ± 1.8 | 6.6 ± 0.9 | 10 ± 1.6 | 0 | 0 | 54.8 ± 1.5 | 5 |
| fab1, fae1 Com25, Com25 | 20.8 ± 0.8 | 32.5 ± 1.7 | 2.5 ± 0.4 | 0.5 ± 0.2 | 1.9 ± 0.7 | 25.5 ± 1.2 | 5.7 ± 1.7 | 11 ± 1.3 | 0 | 0 | 58 ± 1.3 | 8 |
| fab1, fae1 FatB-HPA S | 23.1 ± 1.5 | 4.2 ± 0.6 | 0 | 2.9 ± 0.8 | 36.1 ± 3.9 | 5.1 ± 1.7 | 14.8 ± 1.5 | 13.9 ± 2.3 | 0 | 0 | 9.3 ± 2.0 | 1 |
| fab1, fae1, FatB-HPA S Com25 | 19.1 ± 1.3 | 26.7 ± 2.1 | 0 | 1.9 ± 0.5 | 4.8 ± 1.1 | 28.9 ± 2.3 | 7.8 ± 1.6 | 10.8 ± 2.4 | 0 | 0 | 55.6 ± 1.8 | 6 |
| fab1, fae1 AnΔ9D, LnΔ9d | 12.7 ± 2.1 | 17.9 ± 1.8 | 0.8 ± 0.1 | 0.2 ± 0.1 | 17.7 ± 0.9 | 5.8 ± 0.7 | 24.1 ± 1.2 | 20.8 ± 0.9 | 0 | 0 | 23.7 ± 1.9 | 15 |
| fab1, fae1, Fab1-HPA S Com25, AnΔ9D, LnΔ9d | 11.2 ± 1.3 | 43.4 ± 3.3 | 0.7 ± 0.5 | 0.9 ± 0.2 | 4.6 ± 1.5 | 23.2 ± 1.1 | 8.4 ± 1.2 | 7.6 ± 1.6 | 0 | 0 | 66.6 ± 3.9 | 12 |
| Doxantha | 18.0 ± 0.5 | 54.6 ± 1.7 | 2.4 ± 0.5 | 2.0 ± 0.1 | 1.8 ± 0.2 | 17.3 ± 1.5 | 3.9 ± 0.7 | 0 | 0 | 0 | 71.9 ± 1.3 | n/a |

Levels of 18:1Δ¹ remained the same in the host fab1/fae1/Com25 line, and this line transformed with LnΔ9D and AnΔ9 desaturases (about 25% and about 23%, respectively), which shows that the fae1 mutant is almost entirely devoid in 16:1Δ⁹ elongation activity. This strategy of co-expressing plastidial and extraplastidial desaturases yielded a mean accumulation of about 67% ω-7 FA, with individual plants showing greater than 71%.

What is claimed is:

1. A method for increasing the amount of ω-7 fatty acids in plant material, the method comprising:

transforming plant material with a nucleic acid molecule comprising a polynucleotide that is at least 60% identical to SEQ ID NO:1, wherein the plant material comprises two means for increasing levels of 16:0-ACP in the plant material and an extraplastidial palmitic acid (16:0) desaturase, and wherein the polynucleotide encodes a Δ9 desaturase enzyme comprising an amino acid sequence that is at least 80% identical to SEQ ID NO:2, such that the amount of ω-7 fatty acids in the plant material is increased, thereby producing a transgenic plant material comprising each of:
the polynucleotide,
the Δ9 desaturase enzyme,
the two means for increasing levels of 16:0-ACP in the plant material, and
the extraplastidial palmitic acid (16:0) desaturase.

2. The method of claim 1, wherein the polynucleotide encodes a plastidial delta-9 desaturase having at least 90% identity to SEQ ID NO:2.

3. The method of claim 1, further comprising culturing the transformed plant material to obtain a plant.

4. The method of claim 1, wherein the plant is selected from a genus selected from the group comprising *Arabidopsis, Borago, Brassica, Ricinus, Theobroma, Zea, Gossypium, Crambe, Cuphea, Linum, Lesquerella, Limnanthes,* Linola, *Tropaeolum, Oenothera, Olea, Elaeis, Arachis,* rapeseed, *Carthamus, Glycine, Soja, Helianthus, Nicotiana, Vernonia, Triticum, Hordeum, Oryza, Avena, Sorghum, Secale,* or other members of the Gramineae.

5. The method of claim 1, wherein the plant material is a plant or a seed.

6. The method of claim 1, wherein the nucleic acid molecule of claim 1 further comprises a gene regulatory element.

7. The method of claim 1, wherein the nucleic acid molecule of claim 6, wherein the gene regulatory element is the phaseolin promoter or the LTP170 promoter.

8. The method of claim 1, wherein the Δ9 desaturase enzyme comprises a serine at the position analogous to position 114 in SEQ ID NO:2; an arginine at the position analogous to position 117 in SEQ ID NO:2; a cysteine at the position analogous to position 118 in SEQ ID NO:2, a leucine at the position analogous to position 179 in SEQ ID NO:2; or a threonine at the position analogous to position 188 in SEQ ID NO:2.

9. The method of claim 1, wherein the Δ9 desaturase enzyme comprises a serine at the position analogous to position 114 in SEQ ID NO:2; an arginine at the position analogous to position 117 in SEQ ID NO:2; a cysteine at the position analogous to position 118 in SEQ ID NO:2, a leucine at the position analogous to position 179 in SEQ ID NO:2; and a threonine at the position analogous to position 188 in SEQ ID NO:2.

10. A plant material comprising each of:
two means for increasing levels of 16:0 ACP in the plant material;
an extraplastidial palmitic acid (16:0) desaturase;
a Δ9 desaturase enzyme that comprises an amino acid sequence at least 80% identical to SEQ ID NO:2; and
a polynucleotide is at least 60% identical to SEQ ID NO:1 that encodes the Δ9 desaturase enzyme.

11. The plant material of claim 10, wherein the plant material is a plant.

12. The plant material of claim 10, wherein the plant material is a seed.

13. The method according to claim 1, wherein the extraplastidial palmitic acid (16:0) desaturase is a fungal desaturase.

14. The method according to claim 13, wherein the extraplastidial palmitic acid (16:0) desaturase is selected from the group consisting of LnΔ9D desaturase and AnΔ9 desaturase.

15. The plant material of claim 10, wherein the extraplastidial palmitic acid (16:0) desaturase is a fungal desaturase.

16. The plant material of claim 15, wherein the extraplastidial palmitic acid (16:0) desaturase is selected from the group consisting of LnΔ9D desaturase and AnΔ9 desaturase.

* * * * *

SEQUENCE LISTING

<160> NUMBER OF SEQ ID NOS: 10

<210> SEQ ID NO 1
<211> LENGTH: 1092
<212> TYPE: DNA
<213> ORGANISM: Artificial
<220> FEATURE:
<223> OTHER INFORMATION: Com25 engineered from castor delta9-18:0-desaturase

<400> SEQUENCE: 1

```
gcctctaccc tcaagtctgg ttctaaggaa gttgagaatc tcaagaagcc tttcatgcct      60
cctcgggagg tacatgttca ggttacccat tctatgccac cccaaaagat tgagatcttt     120
aaatccctag acaattgggc tgaggagaac attctggttc atctgaagcc agttgagaaa     180
tgttggcaac cgcaggattt tttgccagat cccgcctctg atggatttga tgagcaagtc     240
agggaactca gggagagagc aaaggagatt cctgatgatt attttgttgt tttggttgga     300
gacatgataa cggaagaagc ccttcccact tatcaaacaa gtctgaatcg ttgtgatgga     360
gttcgggatg aaacaggtgc aagtccgacg tcttgggcaa tttggacaag ggcatggact     420
gcggaagaga atagacatgg tgacctcctc aataagtatc tctacctatc tggacgagtg     480
gacatgaggc aaattgagaa gacaattcaa tatttgattg gttcaggaat ggatttgcgg     540
acagaaaaca gtccatacct tacgttcatc tatacatcat tccaggaaag ggcaaccttc     600
atttctcatg gaacactgc  ccgacaagcc aaagagcatg agacataaa  gttggctcaa     660
atatgtggta caattgctgc agatgagaag cgccatgaga cagcctacac aaagatagtg     720
gaaaaactct ttgagattga tcctgatggt accgttttgg cttttgctga tatgatgaga     780
aagaaaattt ctatgcctgc acacttgatg tatgatggcc gagatgataa tcttttttgac     840
cacttttcag ctgttgcgca gcgtcttgga gtctacacag caaaggatta tgcagatata     900
ttggagttct tggtgggcag atggaaggtg gataaactaa cgggcctttc agctgaggga     960
caaaaggctc aggactatgt ttgtcggtta cctccaagaa ttagaaggct ggaagagaga    1020
gctcaaggaa gggcaaagga agcacccacc atgcctttca gctggatttt cgataggcaa    1080
gtgaagctgt ag                                                       1092
```

<210> SEQ ID NO 2
<211> LENGTH: 363
<212> TYPE: PRT
<213> ORGANISM: Artificial
<220> FEATURE:
<223> OTHER INFORMATION: Com25 engineered from castor delta9-18:0-desaturase

<400> SEQUENCE: 2

```
Ala Ser Thr Leu Lys Ser Gly Ser Lys Glu Val Glu Asn Leu Lys Lys
1               5                   10                  15

Pro Phe Met Pro Pro Arg Glu Val His Val Gln Val Thr His Ser Met
            20                  25                  30

Pro Pro Gln Lys Ile Glu Ile Phe Lys Ser Leu Asp Asn Trp Ala Glu
        35                  40                  45

Glu Asn Ile Leu Val His Leu Lys Pro Val Glu Lys Cys Trp Gln Pro
    50                  55                  60
```

Gln Asp Phe Leu Pro Asp Pro Ala Ser Asp Gly Phe Asp Glu Gln Val
65                  70                  75                  80

Arg Glu Leu Arg Glu Arg Ala Lys Glu Ile Pro Asp Tyr Phe Val
                85                  90                  95

Val Leu Val Gly Asp Met Ile Thr Glu Glu Ala Leu Pro Thr Tyr Gln
            100                 105                 110

Thr Ser Leu Asn Arg Cys Asp Gly Val Arg Asp Glu Thr Gly Ala Ser
                115                 120                 125

Pro Thr Ser Trp Ala Ile Trp Thr Arg Ala Trp Thr Ala Glu Glu Asn
            130                 135                 140

Arg His Gly Asp Leu Leu Asn Lys Tyr Leu Tyr Leu Ser Gly Arg Val
145                 150                 155                 160

Asp Met Arg Gln Ile Glu Lys Thr Ile Gln Tyr Leu Ile Gly Ser Gly
                165                 170                 175

Met Asp Leu Arg Thr Glu Asn Ser Pro Tyr Leu Thr Phe Ile Tyr Thr
            180                 185                 190

Ser Phe Gln Glu Arg Ala Thr Phe Ile Ser His Gly Asn Thr Ala Arg
                195                 200                 205

Gln Ala Lys Glu His Gly Asp Ile Lys Leu Ala Gln Ile Cys Gly Thr
210                 215                 220

Ile Ala Ala Asp Glu Lys Arg His Glu Thr Ala Tyr Thr Lys Ile Val
225                 230                 235                 240

Glu Lys Leu Phe Glu Ile Asp Pro Asp Gly Thr Val Leu Ala Phe Ala
                245                 250                 255

Asp Met Met Arg Lys Lys Ile Ser Met Pro Ala His Leu Met Tyr Asp
                260                 265                 270

Gly Arg Asp Asp Asn Leu Phe Asp His Phe Ser Ala Val Ala Gln Arg
                275                 280                 285

Leu Gly Val Tyr Thr Ala Lys Asp Tyr Ala Asp Ile Leu Glu Phe Leu
            290                 295                 300

Val Gly Arg Trp Lys Val Asp Lys Leu Thr Gly Leu Ser Ala Glu Gly
305                 310                 315                 320

Gln Lys Ala Gln Asp Tyr Val Cys Arg Leu Pro Pro Arg Ile Arg Arg
                325                 330                 335

Leu Glu Glu Arg Ala Gln Gly Arg Ala Lys Glu Ala Pro Thr Met Pro
                340                 345                 350

Phe Ser Trp Ile Phe Asp Arg Gln Val Lys Leu
            355                 360

<210> SEQ ID NO 3
<211> LENGTH: 31
<212> TYPE: DNA
<213> ORGANISM: Artificial
<220> FEATURE:
<223> OTHER INFORMATION: P17-5'BamHI primer

<400> SEQUENCE: 3
gggatccccg ggttgacatt tttaccttt t                                31

<210> SEQ ID NO 4
<211> LENGTH: 27
<212> TYPE: DNA
<213> ORGANISM: Artificial
<220> FEATURE:
<223> OTHER INFORMATION: P17-3'PacI primer

<400> SEQUENCE: 4

```
ggttaattaa gtcttcaaac tctagga                                          27

<210> SEQ ID NO 5
<211> LENGTH: 32
<212> TYPE: DNA
<213> ORGANISM: Artificial
<220> FEATURE:
<223> OTHER INFORMATION: FatB-hps-5'PstI primer

<400> SEQUENCE: 5
gggctgcaga aacaagtttc ggccaccaac cc                                    32

<210> SEQ ID NO 6
<211> LENGTH: 29
<212> TYPE: DNA
<213> ORGANISM: Artificial
<220> FEATURE:
<223> OTHER INFORMATION: FatB-hps-3'XhoI primer

<400> SEQUENCE: 6
cccctcgaga catcagaatt cgtaatgat                                        29

<210> SEQ ID NO 7
<211> LENGTH: 28
<212> TYPE: DNA
<213> ORGANISM: Artificial
<220> FEATURE:
<223> OTHER INFORMATION: FatB-hpa-5'NheI primer

<400> SEQUENCE: 7
ggggctagca agtttcggcc accaaccc                                         28

<210> SEQ ID NO 8
<211> LENGTH: 31
<212> TYPE: DNA
<213> ORGANISM: Artificial
<220> FEATURE:
<223> OTHER INFORMATION: FatB-hpa-3'PacI primer

<400> SEQUENCE: 8
cccttaatta aacatcagaa ttcgtaatga t                                     31

<210> SEQ ID NO 9
<211> LENGTH: 34
<212> TYPE: DNA
<213> ORGANISM: Artificial
<220> FEATURE:
<223> OTHER INFORMATION: FatB-Exon-5'Sp-Bam primer

<400> SEQUENCE: 9
ccactagtgg atccacctct gctacgtcgt catt                                  34

<210> SEQ ID NO 10
<211> LENGTH: 34
<212> TYPE: DNA
<213> ORGANISM: Artificial
<220> FEATURE:
<223> OTHER INFORMATION: FatB-Exon-3'Bg-Sal primer

<400> SEQUENCE: 10
ggagatctgt cgacgtagtt atagcagcaa gaag                                  34
```